(12) United States Patent
Karsenty et al.

(10) Patent No.: US 12,280,115 B2
(45) Date of Patent: Apr. 22, 2025

(54) CYTOKINE-BISPHOSPHONATE CONJUGATES

(71) Applicants: The Trustees of Columbia University in the City of New York, New York, NY (US); William Marsh Rice University, Houston, TX (US)

(72) Inventors: Gerard Karsenty, New York, NY (US); Julian Berger, New York, NY (US); Han Xiao, Houston, TX (US)

(73) Assignees: The Trustees of Columbia University in the City of New York, New York, NY (US); William Marsh Rice University, Houston, TX (US)

( * ) Notice: Subject to any disclaimer, the term of this patent is extended or adjusted under 35 U.S.C. 154(b) by 0 days.

(21) Appl. No.: 18/630,263

(22) Filed: Apr. 9, 2024

(65) Prior Publication Data

US 2024/0269294 A1    Aug. 15, 2024

Related U.S. Application Data

(63) Continuation of application No. PCT/US2022/077956, filed on Oct. 12, 2022.

(60) Provisional application No. 63/255,104, filed on Oct. 13, 2021.

(51) Int. Cl.
*A61K 47/54* (2017.01)
*A61P 21/00* (2006.01)

(52) U.S. Cl.
CPC .......... *A61K 47/548* (2017.08); *A61K 47/545* (2017.08); *A61P 21/00* (2018.01)

(58) Field of Classification Search
None
See application file for complete search history.

(56) References Cited

U.S. PATENT DOCUMENTS

| 2016/0095932 A1 | 4/2016 | Karpeisky et al. |
| 2017/0319605 A1 | 11/2017 | Lisignoli et al. |
| 2019/0038749 A1 | 2/2019 | Grubbs et al. |
| 2020/0188484 A1 | 6/2020 | Ptacin et al. |

FOREIGN PATENT DOCUMENTS

| WO | WO-2011007135 A1 * | 1/2011 | ........... A61K 31/155 |
| WO | WO-2020069319 A1 * | 4/2020 | ........... A61K 31/663 |
| WO | 2021016583 A1 | 1/2021 | |

OTHER PUBLICATIONS

International Search Report and Written Opinion dated Jan. 20, 2023, issued in PCT International Appln. PCT/US2022/077956.
Mbese et al., "Bisphosphonate-Based Conjugates and Derivatives as Potential Therapeutic Agents in Osteoporosis, Bone Cancer and Metastatic Bone Cancer," Intl. Journal of Molecular Sciences, vol. 22, No. 6869, Jun. 26, 2021, 21 pages.

* cited by examiner

*Primary Examiner* — Brian Gangle
*Assistant Examiner* — Andrea K McCollum
(74) *Attorney, Agent, or Firm* — Amster, Rothstein & Ebenstein LLP

(57) ABSTRACT

Cytokine-bisphosphonate conjugates and methods of use thereof in muscle functions.

7 Claims, 14 Drawing Sheets

Specification includes a Sequence Listing.

CYTOKINE-BISPHOSPHONATE CONJUGATES

CROSS-REFERENCE TO RELATED APPLICATIONS

This application is a continuation of PCT International Application No. PCT/US2022/077956, filed Oct. 12, 2022, which claims benefit of U.S. Provisional Application No. 63/255,104, filed Oct. 13, 2021, the contents of which are hereby incorporated by reference.

STATEMENT OF GOVERNMENTAL INTEREST

This invention was made with government support under grant AR073180 awarded by the National Institutes of Health. The government has certain rights in the invention.

SEQUENCE LISTING

"2022_10_07_93597_6457_Sequence_Listing_RRS.xml", created on Oct. 7, 2022 in the ST26 sequence format, submitted electronically using the Patent Center, as the Sequence Listing XML for the subject application.

BACKGROUND

The disclosures of all publications, patents, patent application publications and books referred to in this application are hereby incorporated by reference in their entirety into the subject application to more fully describe the art to which the subject invention pertains.

A decline in muscle function is a devastating manifestation of aging that limits the ability of affected individuals to walk and perform elementary tasks. Due to the health benefits of exercise, this decline also has an indirect negative consequence on many other physiologies. Osteocalcin (OCN) is a bone-derived hormone that is necessary and sufficient to increase muscle function. Osteocalcin levels decline precipitously with age and accordingly replenishing OCN levels in aged mice restores their exercise capacity to youthful levels. However, to have this effect in a human, OCN must be continuously perfused by implanted pump due to its short half-life, which limits its development as a drug.

Accordingly, there may be a need to address and/or at least partially overcome at least some of the prior deficiencies described herein.

SUMMARY OF THE INVENTION

Disclosed herein is a method for inhibiting, reducing and/or treating loss of muscle function. Such a method can comprise, e.g., administering to a subject a pharmaceutical composition comprising a therapeutically effective amount of an agent that enhances Interleukin-6 (IL) release or activity, e.g., during or prior to exercise, and optionally a pharmaceutically acceptable carrier or excipient. For example, the subject can suffer from sarcopenia, or loss of exercise capacity. The treatment can help restore exercise capacity and/or reduce effects of sarcopenia. In addition, or alternatively, the subject can suffer from at least one condition selected from the group consisting of hip fracture, cancer, liver cirrhosis, Cushing's syndrome, Duchenne muscular dystrophy, a mitochondrial disease, kidney failure, diabetes and aging. In certain exemplary embodiments of the present disclosure, the agent can further inhibit or treat loss of muscle mass.

According to certain exemplary embodiments of the present disclosure, it is possible to utilize an agent as described herein that enhances Interleukin-6 (IL) release or activity for inhibiting or treating loss of muscle function. In other exemplary embodiments of the present disclosure, it is possible to use an agent as described herein that enhances Interleukin-6 (IL) release or activity in manufacturing a medicament for inhibiting or treating loss of muscle function.

In certain exemplary embodiments of the present disclosure, the exemplary agent can be an IL-6 family cytokine conjugated to a bisphosphonate (IL6-BP).

An IL-6 family cytokine-bisphosphonate conjugate is provided comprising a bisphosphonate attached via one of its non-phosphonate R groups through a linking portion to a an IL-6 family cytokine.

An IL-6 family cytokine-bisphosphonate conjugate is provided having the structure:

a)

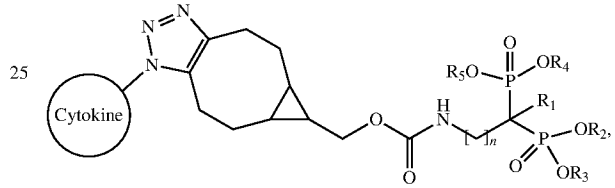

wherein
the cytokine comprises an azidophenylalanine residue, wherein the triazole set forth above is composed from an azide group of the azidophenylalanine residue, and wherein $$n = 1 \text{ to } 10$$

$R_1$=H, OH, a halogen, CN, COOH, $CONH_2$, an alkyl ester, an optionally substituted alkyl, an optionally substituted aryl, or an optionally substituted heteroaryl and $R_2$, $R_3$, $R_4$, $R_5$ are each independently H, an optionally substituted alkyl, an optionally substituted aryl, or an optionally substituted heteroaryl;

or
b)

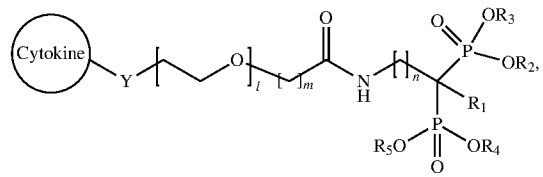

wherein
the cytokine comprises a native lysine residue, and wherein Y comprises a nitrogen of a sidechain of the native lysine residue and wherein Y is an alkylimine, an amide, a urea, thiourea, a sulfamidate, a substituted benzo[d][1,2,3]triazin-4(3H)-one, or a substituted 2-alkyliminoboronic acid, and wherein
when Y is an alkylimine, the bisphosphonate is attached via an imine carbon atom and the cytokine is attached at the nitrogen atom, or
when Y is an amide, the bisphosphonate is attached via a carbonyl carbon atom of the amide and the cytokine is attached via a nitrogen atom of the amide, or
when Y is a urea, the bisphosphonate is attached to one of the nitrogen atoms thereof and the cytokine is attached at the other nitrogen atom, or
when Y is a thiourea, the bisphosphonate is attached to one of the nitrogen atoms thereof and the cytokine is attached at the other nitrogen atom, or
when Y is a sulfamidate, the bisphosphonate is attached at one of the oxygen atoms thereof, and the cytokine is attached at the nitrogen atom, or
when Y is a substituted benzo[d][1,2,3]triazin-4(3H)-one, the bisphosphonate is attached at the 5, 6, 7, or 8 position and the cytokine is attached at the nitrogen atom alpha to the carbonyl,
and
wherein l=0 to 12, m=0 to 8, and n=1 to 10;
or a pharmaceutically-acceptable salt thereof,
wherein the cytokine is an IL-6, Leptin, IL-11, ciliary neurotrophic factor (CNTF), leukemia inhibitory factor (LIF), oncostatin M (OSM), cardiotrophin 1 (CT-1), cardiotrophin-like cytokine (CLC), or IL-27.

A method of treating or reducing loss of muscle function in a subject is provided comprising administering an amount of any of the IL-6 family cytokine-bisphosphonate conjugate as described herein to the subject in an amount effective to treat or reduce loss of muscle function.

A method of increasing exercise capacity in a subject is provided having sarcopenia comprising administering an amount of any of the IL-6 family cytokine-bisphosphonate conjugates as described herein to the subject in an amount effective to increase exercise capacity.

A compound is provided having the structure:

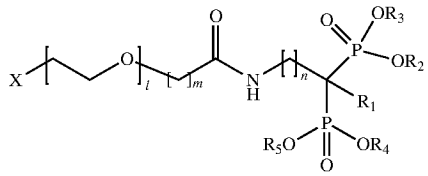

wherein $l = 0$ to 12, $m = 0$ to 8, and $n = 1$ to 10 and
$R_1$=H, OH, a halogen, CN, COOH, $CONH_2$, an alkyl ester, an optionally substituted alkyl, an optionally substituted aryl, or an optionally substituted heteroaryl
and
$R_2$, $R_3$, $R_4$, $R_5$ are each independently H, an optionally substituted alkyl, an optionally substituted aryl, or an optionally substituted heteroaryl
and
X=CHO, —N=C=S, —O—$SO_2$F, an NHS ester, a substituted ortho-carbonylboronic acid, a substituted ortho-(methoxycarbonyl)benzenediazonium, or 9-methoxybicyclo[6.1.0]non-4-yne.

BRIEF DESCRIPTION OF THE DRAWINGS

FIG. 9A illustrates an exemplary graph of a preventative experimental model with Dex or Vehicle delivering mini-pump was implanted at Day 0, at Day 0 mice also receive one of the following mini-pump treatments: Vehicle, VK5211 (selective androgen receptor modulator), EPO (erythropoietin) or Ocn (osteocalcin), after 27 days all mice were tested for muscle function during aerobic exercise by recording time and distance until exhaustion when forced to run at constant speed on a treadmill, and then at day 28, all mice were sacrificed and their soleus muscle was collected for molecular analysis; FIG. 9B showing an exemplary graph of time and distance until exhaustion from running on treadmill; FIG. 9C illustrates an exemplary graph of IL-6 expression by RT-PCR in soleus muscle at day 28 of experiment.

DETAILED DESCRIPTION

Figure 1:
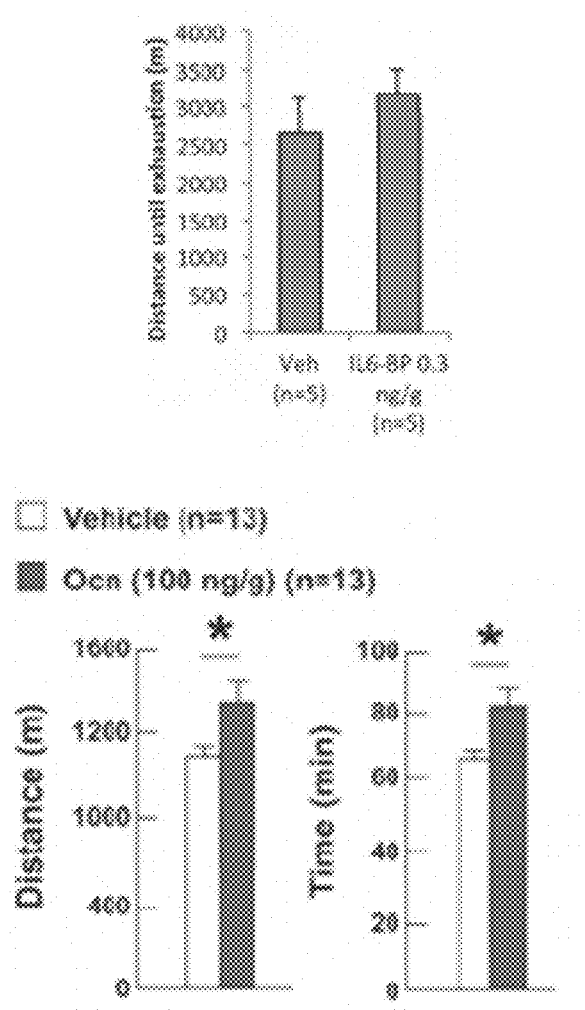
FIG. 1 is an exemplary graph showing the effect of an interleukin-6-BP conjugate (IL6-BP) injection (30 minutes post injection) on exercise capacity at 3-month old.
Figure 2:
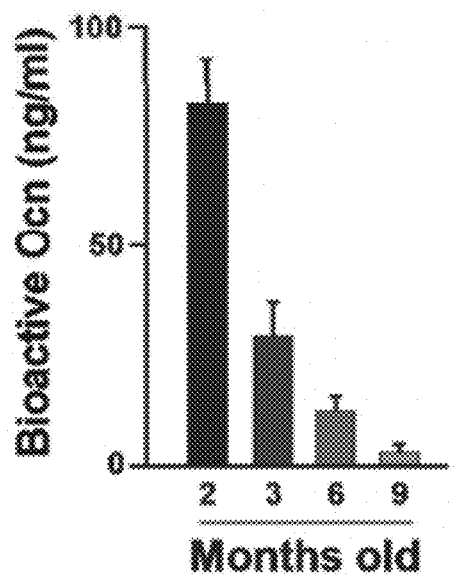
FIG. 2 shows bioactive OCN levels in mice of varying ages and also shows exercise capacity (time running on treadmill until exhaustion) of mice 30 minutes after injection of IL6-BP or vehicle control intraperitoneally, whereas exercise protocol is 5 minutes at 8 cm/s, 5 minutes at 16 cm/s, increase of 2 cm/s each minute until a speed of 30 cm/s and then running at 30 cm/s until exhaustion. Distance in cm.
Figure 2:
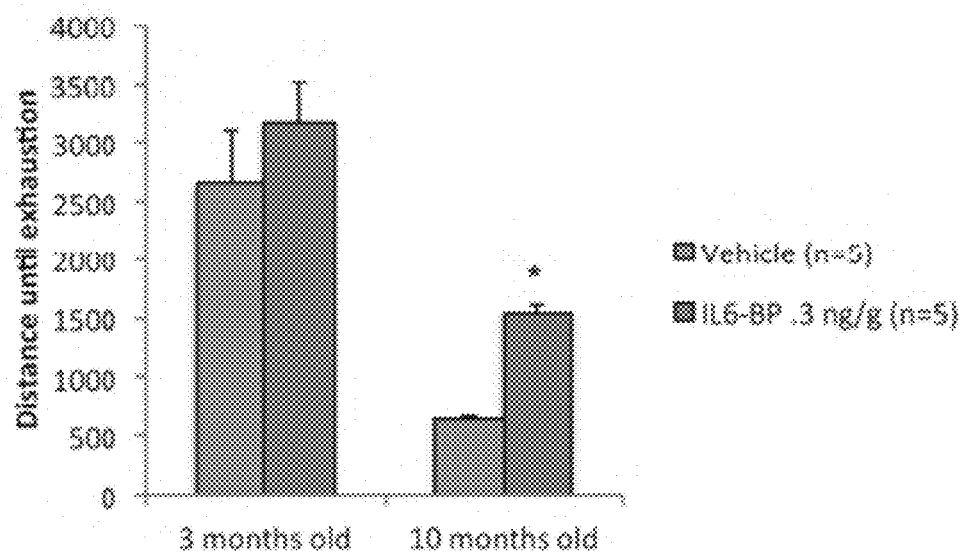
Figure 3:
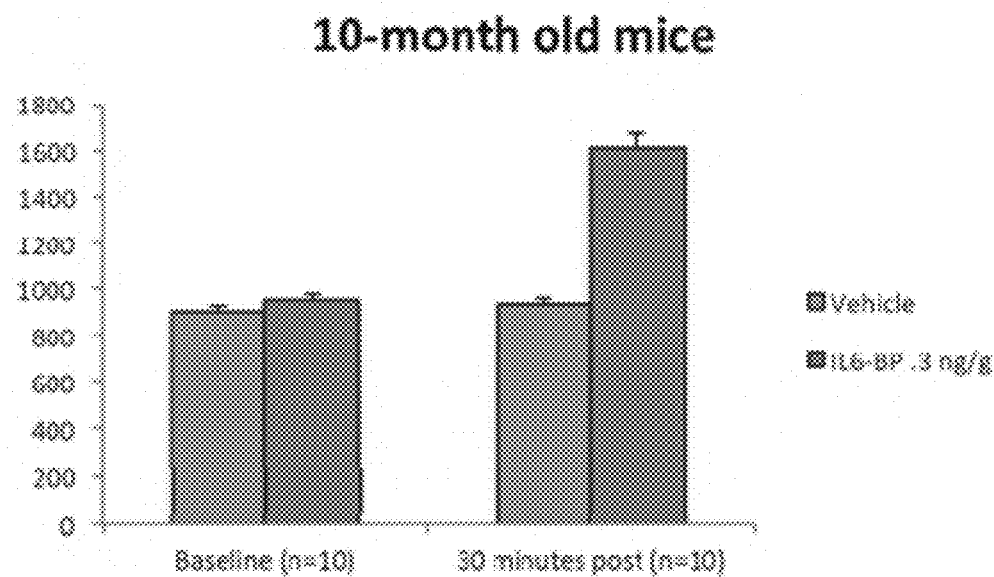
FIG. 3 is a bar chart showing exercise capacity (time running on treadmill until exhaustion) of 10-month old mice at baseline and at 30 minutes after injection of IL6-BP or vehicle control intraperitoneally, whereas exercise protocol is 5 minutes at 8 cm/s, 5 minutes at 16 cm/s, increase of 2 cm/s each minute until a speed of 30 cm/s and then running at 30 cm/s until exhaustion. Distance in cm.
Figure 4:
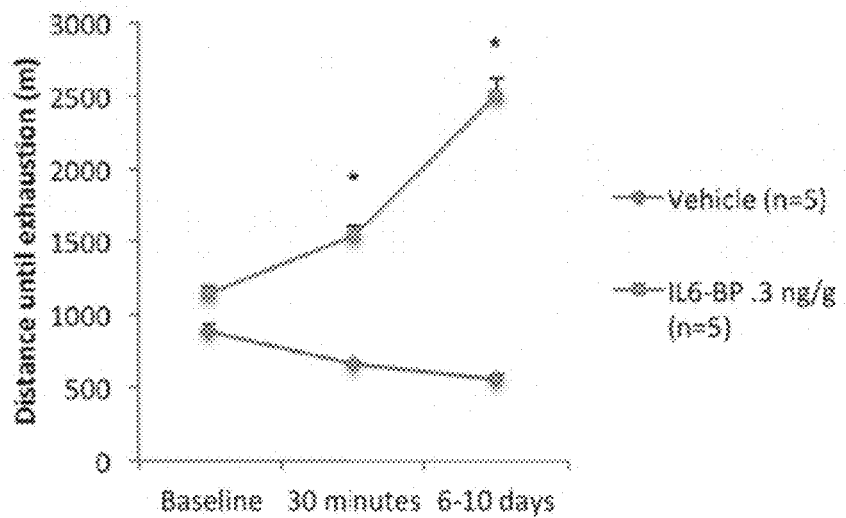
FIG. 4 is an exemplary graph showing exercise capacity (time running on treadmill until exhaustion) of mice at indicated time points after injection of IL6-BP or vehicle control intraperitoneally, whereas exercise protocol is 5 minutes at 8 cm/s, 5 minutes at 16 cm/s, increase of 2 cm/s each minute until a speed of 30 cm/s and then running at 30 cm/s until exhaustion.
Figure 5:
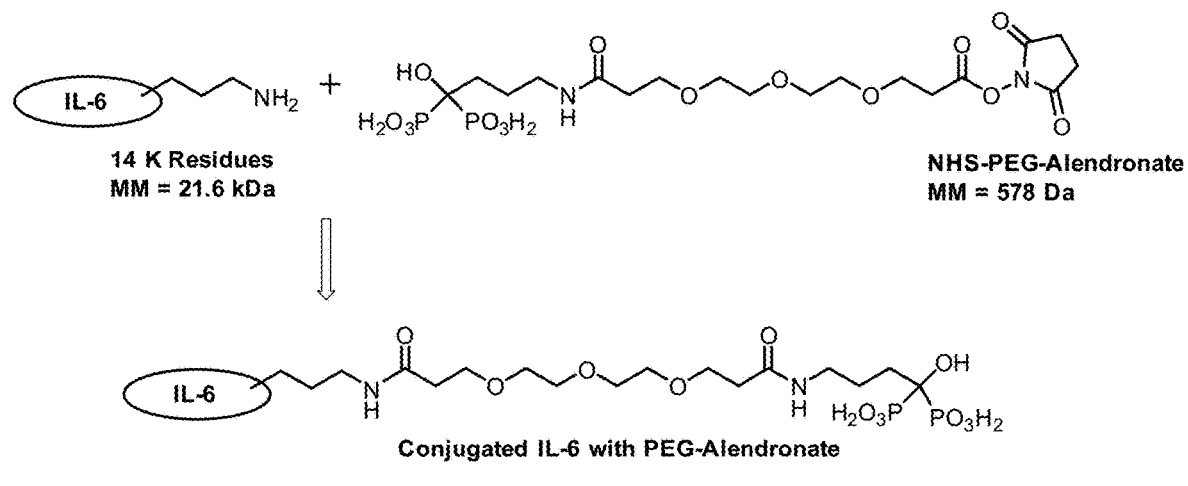
FIG. 5 is a schematic representation of an exemplary 1st generation IL6-BP conjugate used in exemplary experiments where alendronate was pegylated and an NHS moiety was attached, the NHS-PEG-alendronate molecule was bound to IL6 by Lysine conjugation, and the IL6 fused to alendronate is an exemplary 1st generation IL6-BP and so targets IL6 signaling to bone.
Figure 6:
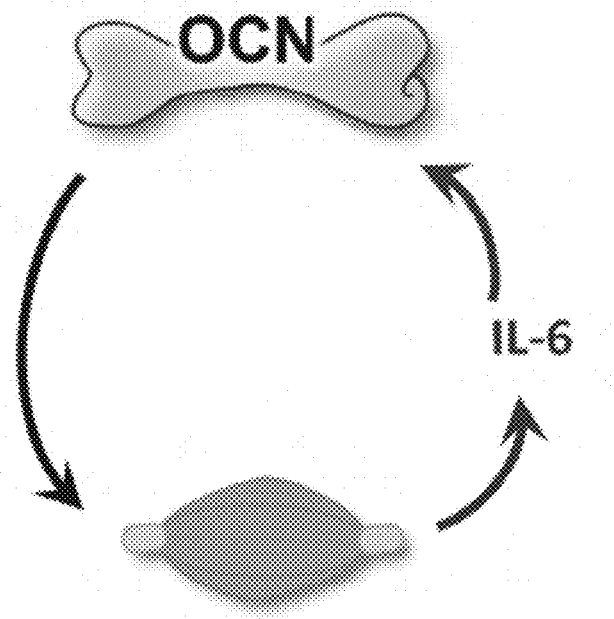
FIG. 6 is a schematic representation of an exemplary endocrine loop that exists between bone and muscle and is activated during exercise, whereas in under 10 minutes after onset of exercise osteocalcin is released from bone into blood circulation, osteocalcin signaling in muscle cells can increase ATP production and the release of IL6 from muscle, IL6 from muscle travels to bone where it further stimulates the release of osteocalcin from bone, with this feed forward loop being possible to be required for exercise.
Figure 7:
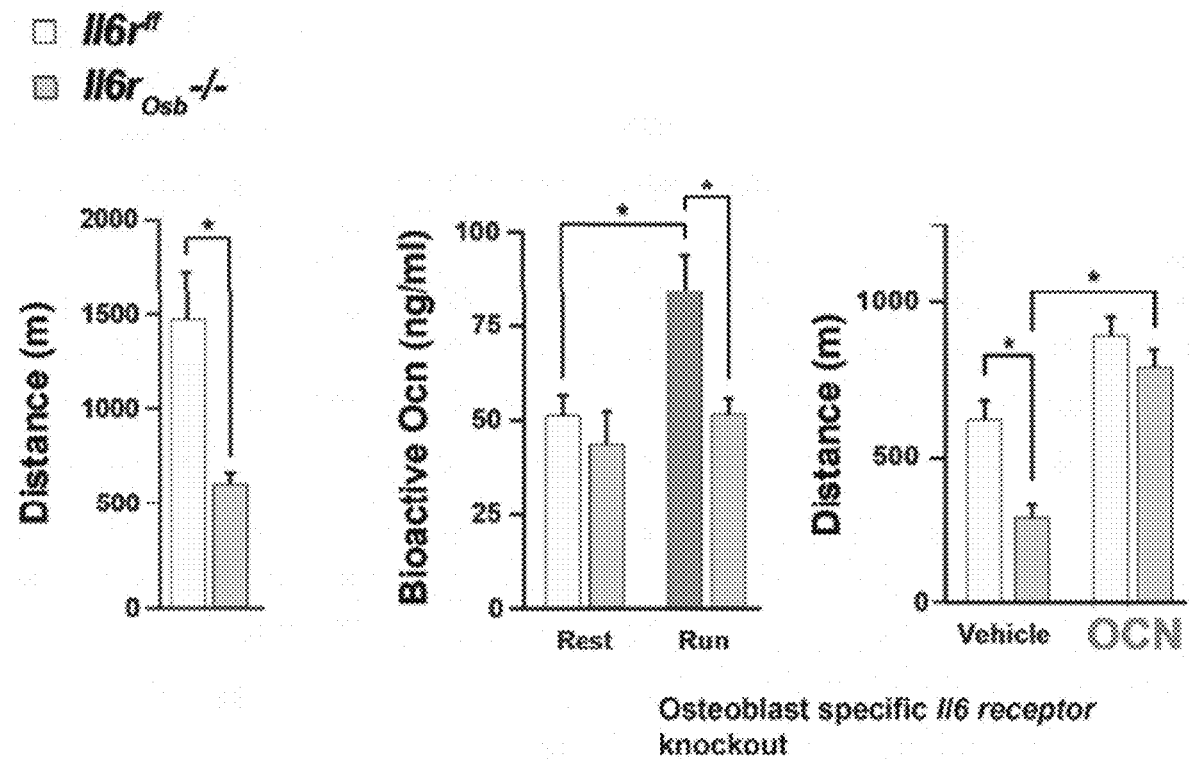
FIG. 7 is a set of exemplary graphs showing that mice with a conditional deletion of the IL6 receptor (IL6ra flox mice crossed with Ostecalcin-cre mice) in osteoblasts have diminished exercise capacity, no increase in osteocalcin after exercise, whereas replenishing osteocalcin in these mutant mice increase their exercise capacity which demonstrates that IL6 signaling in bone is required for exercise and acts at least in part by increasing osteocalcin release from bone.
Figure 8:
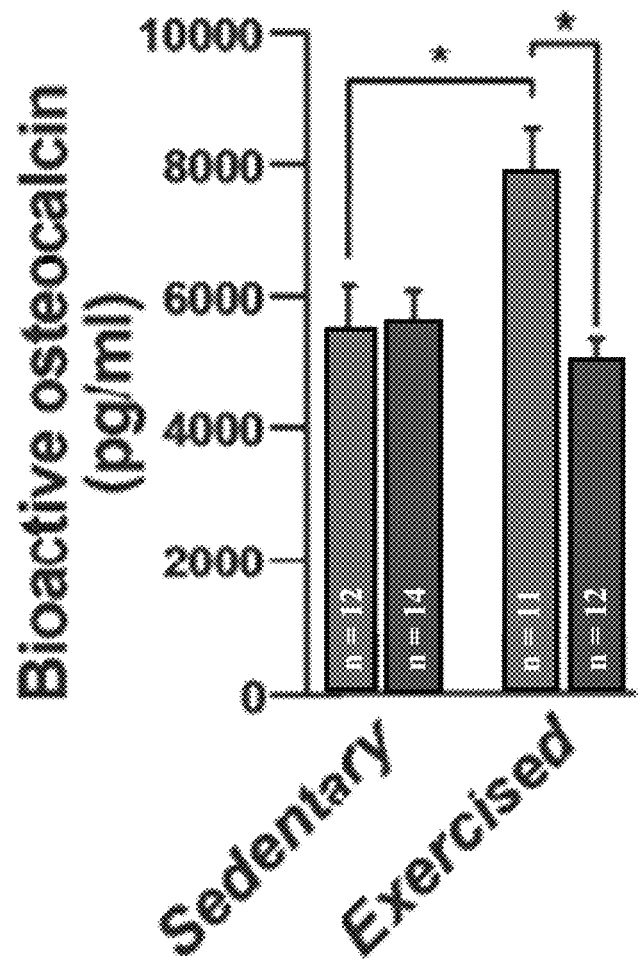
FIG. 8 is an exemplary graph showing that human that were exercised exhibited an increase in osteocalcin in the blood, as observed in mice, whereas an experimental group of humans that were treated with an IL6 receptor inhibitory antibody (Tocilizumab) did not increase their osteocalcin levels in response to exercise. This shows that the IL6-dependent release of osteocalcin during exercise also occurs in humans.

An IL-6 family cytokine-bisphosphonate conjugate comprising a bisphosphonate attached via one of its non-phosphonate R groups through a linking portion to an IL-6 family cytokine. The IL-6 family cytokines are IL-6, Leptin, IL-11, ciliary neurotrophic factor (CNTF), leukemia inhibitory factor (LIF), oncostatin M (OSM), cardiotrophin 1 (CT-1), cardiotrophin-like cytokine (CLC), or IL-27. In embodiments, the IL-6 family cytokine has the sequence of the human IL-6 family cytokine (bar any substitutions with, e.g., an azidophenylalanine as described herein). In embodiments, the bisphosphonate is attached via one of its non-phosphonate R groups through an NHS ester to a cytokine. In embodiments, the bisphosphonate is attached via one of its non-phosphonate R groups through the linker portion to a lysine residue of the cytokine. In embodiments, the bisphosphonate is attached via one of its non-phosphonate R groups through the linker portion to a cysteine residue of the cytokine. In embodiments, the bisphosphonate is attached via one of its non-phosphonate R groups through the linker portion to a non-canonical amino acid residue incorporated into the cytokine. In embodiments, the non-canonical residue is an azidophenylalanine residue. In embodiments the cytokine is interleukin-6. In embodiments, the bisphosphonate is attached via one of its non-phosphonate R groups through an NHS ester to an interleukin-6. In embodiments, the bisphosphonate is attached via one of its non-phosphonate R groups through the linker portion to a lysine residue of the interleukin-6. In embodiments, the bisphosphonate is attached via one of its non-phosphonate R groups through the linker portion to a cysteine residue of the interleukin-6. In embodiments, the bisphosphonate is attached via one of its non-phosphonate R groups through the linker portion to a non-canonical amino acid residue incorporated into the interleukin-6. In embodiments, the non-canonical residue is an azidophenylalanine residue. In embodiments, the linking portion comprises a click chemistry or a pClick chemistry linker.

A cytokine-bisphosphonate conjugate having the structure:

a)

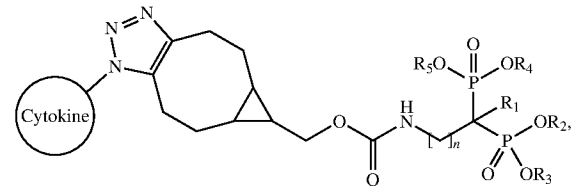

wherein
the cytokine comprises an azidophenylalanine residue, wherein the triazole set forth above is composed from an azide group of the azidophenylalanine residue, and wherein $n = 1$ to $10$ $R_1$=H, OH, a halogen, CN, COOH, CONH$_2$, an alkyl ester, an optionally substituted alkyl, an optionally substituted aryl, or an optionally substituted heteroaryl and $R_2$, $R_3$, $R_4$, $R_5$ are each independently H, an optionally substituted alkyl, an optionally substituted aryl, or an optionally substituted heteroaryl;

or b)

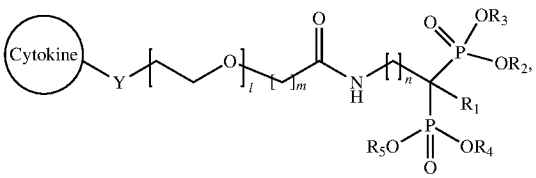

wherein
the cytokine comprises a native lysine residue, and wherein Y comprises a nitrogen of a sidechain of the native lysine residue and wherein Y is an alkylimine, an amide, a urea, thiourea, a sulfamidate, a substituted benzo[d][1,2,3]triazin-4(3H)-one, or a substituted 2-alkyliminoboronic acid, and wherein when Y is an alkylimine, the bisphosphonate is attached via an imine carbon atom and the cytokine is attached at the nitrogen atom, or when Y is an amide, the bisphosphonate is attached via a carbonyl carbon atom of the amide and the cytokine is attached via a nitrogen atom of the amide, or when Y is a urea, the bisphosphonate is attached to one of the nitrogen atoms thereof and the cytokine is attached at the other nitrogen atom, or when Y is a thiourea, the bisphosphonate is attached to one of the nitrogen atoms thereof and the cytokine is attached at the other nitrogen atom, or when Y is a sulfamidate, the bisphosphonate is attached at one of the oxygen atoms thereof, and the cytokine is attached at the nitrogen atom, or when Y is a substituted benzo[d][1,2,3]triazin-4(3H)-one, the bisphosphonate is attached at the 5, 6, 7, or 8 position and the cytokine is attached at the nitrogen atom alpha to the carbonyl, and wherein l=0 to 12, m=0 to 8, and n=1 to 10;

or a pharmaceutically-acceptable salt thereof, wherein the cytokine is an IL-6, Leptin, IL-11, ciliary neurotrophic factor (CNTF), leukemia inhibitory factor (LIF), oncostatin M (OSM), cardiotrophin 1 (CT-1), cardiotrophin-like cytokine (CLC), or IL-27.

In embodiments, the cytokine-bisphosphonate conjugate comprises the following molecule, or pharmaceutically acceptable salt thereof, wherein IL-6 is an interleukin-6:

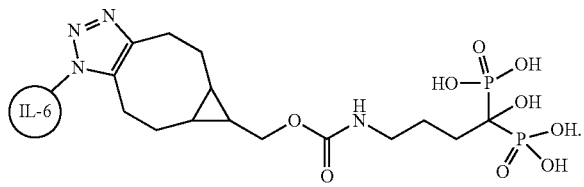 [SMILES: Cn1nnc2c1CCC1C(CC2)C1COC(=O)NCCCC(O)(P(=O)(O)O)P(=O)(O)O]

In embodiments, the cytokine-bisphosphonate conjugate comprises the following molecule, or pharmaceutically acceptable salt thereof, wherein IL-6 is an interleukin-6:

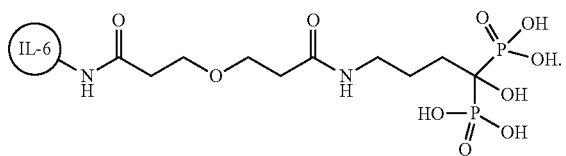 [SMILES: CNC(=O)CCOCCC(=O)NCCCC(O)(P(=O)(O)O)P(=O)(O)O]

In embodiments, the IL-6 is substituted with another IL-6 family cytokine member, namely, Leptin, IL-11, ciliary neurotrophic factor (CNTF), leukemia inhibitory factor (LIF), oncostatin M (OSM), cardiotrophin 1 (CT-1), cardiotrophin-like cytokine (CLC), or IL-27.

In embodiments, the azidophenylalanine is incorporated at a Phe9, Phe14, Phe25, Tyr46, Thr20, Lys68, Glu74, Ser75, Thr82, Asn131, Ala134, Thr137, Thr141, Ser145, Thr148, Lys149, Glu151, or Leu180 residue of the Interleukin-6.

In an embodiment, the Interleukin-6 has the following sequence:

(SEQ ID NO: 1)
MNSFSTSAFGPVAFSLGLLLVLPAAFPAPVPPGEDSKDVAAPHRQPLTS

SERIDKQIRYILDGISALRKETCNKSNMCESSKEALAENNLNLPKMAEK

DGCFQSGFNEETCLVKIITGLLEFEVYLEYLQNRFESSEEQARAVQMST

KVLIQFLQKKAKNLDAITTPDPTTNASLLTKLQAQNQWLQDMTTHLILR

SFKEFLQSSLRALRQM.

In embodiments the azidophenylalanine is incorporated at Phe9, Phe14, Phe25, Thr48, Lys69, Ser 75, Asn131, Ala140, Ser146, Thr 147, Lys150, Leu179 or of a human IL-6 sequence.

In an embodiment, the IL-6 has the sequence of Human Uniprot P05231. A human Uniprot P05231 sequence is shown below with underlined residues show non-limiting examples of residues suitable for substitution by azidophenylalanine:

(SEQ ID NO: 2)
MNSFSTSA<u>F</u>GPVA<u>F</u>SLGLLLVLPAA<u>F</u>PAPVPPGEDSKDVAAPHRQPL<u>TS</u>

SERIDKQIRYILDGISAL<u>R</u>KETCNK<u>S</u>NMCESSKEALAENNLNLPKMAEK

DGCFQSGFNEETCLVKIITGLLEFEVYLEYLQ<u>N</u>RFESSEE<u>Q</u>ARAVQ<u>MST</u>

KVL<u>I</u>QFLQ<u>K</u>KAKNLDAITTPDPTTNASLLT<u>K</u>LQAQNQWLQDMTTHLILR

SFKEFLQSSLRALRQM

In embodiments, the azidophenylalanine is functionalized with a bicyclo [6.1.0] nonyne-bisphosphonate.

In embodiments, the bisphosphonate is a non-nitrogenous bisphosphonate.

In embodiments, the bisphosphonate is a nitrogenous bisphosphonate.

In embodiments, the bisphosphonate Alendronate.

In embodiments, the bisphosphonate is Etidronate, Tiludronate, Pamidronate, Neridronate, Olpadronate, Ibandronate, Risedronate, or Zoledronate.

In embodiments, the cytokine-bisphosphonate conjugate comprises only one bisphosphonate.

In embodiments, the cytokine of the cytokine-bisphosphonate is an interleukin-6. In embodiments the interleukin-6 has the sequence of a human interleukin-6. In embodiments, the interleukin-6 has the sequence of Uniprot Accession no. P05231.

Also provided is a method of treating or reducing loss of muscle function in a subject comprising administering an amount of any of the cytokine-bisphosphonate conjugates described herein to the subject in an amount effective to treat or reduce loss of muscle function.

A method of increasing exercise capacity in a subject having sarcopenia comprising administering an amount of any of the cytokine-bisphosphonate conjugates described herein to the subject in an amount effective to increase exercise capacity.

Also provided is a method of treating or reducing loss of muscle function in a subject comprising administering an amount of any of the interleukin-6-bisphosphonate conjugates described herein to the subject in an amount effective to treat or reduce loss of muscle function.

A method of increasing exercise capacity in a subject having sarcopenia comprising administering an amount of any of the interleukin-6-bisphosphonate conjugates described herein to the subject in an amount effective to increase exercise capacity.

In embodiments, the amount of cytokine-bisphosphonate conjugate is administered to the subject prior to exercise. In embodiments, the amount of interleukin-6-bisphosphonate conjugate is administered to the subject during exercise.

In embodiments, an amount of

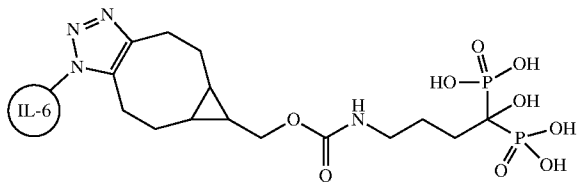 [SMILES: Cn1nnc2c1CCC1C(CC2)C1COC(=O)NCCCC(O)(P(=O)(O)O)P(=O)(O)O]

is administered, wherein IL-6 is interleukin-6.

In embodiments, an amount of

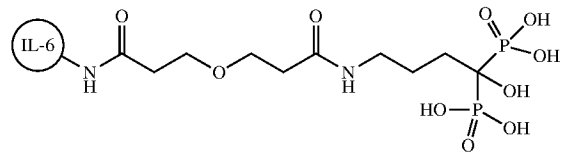 [SMILES: CNC(=O)CCOCCC(=O)NCCCC(O)(P(=O)(O)O)P(=O)(O)O]

is administered, wherein IL-6 is interleukin-6.

In embodiments, the subject has loss of muscle function associated with aging.

In embodiments, the subject has sarcopenia.

In embodiments, the subject has suffered from or has a hip fracture, cancer, liver cirrhosis, Cushing's syndrome, Duchenne muscular dystrophy, a mitochondrial disease, a kidney failure, osterosarcopenia or diabetes.

In embodiments, the method further comprises diagnosing the subject as suffering from a loss of muscle function or exercise capacity loss prior to administering the composition to the subject.

In embodiments, the subject is a human subject.

In embodiments, the subject is 60 years or older.

In embodiments, the cytokine-bisphosphonate conjugate is an interleukin-6-bisphosphonate conjugate.

Also provided is a bisphosphonate conjugate having the following structure:

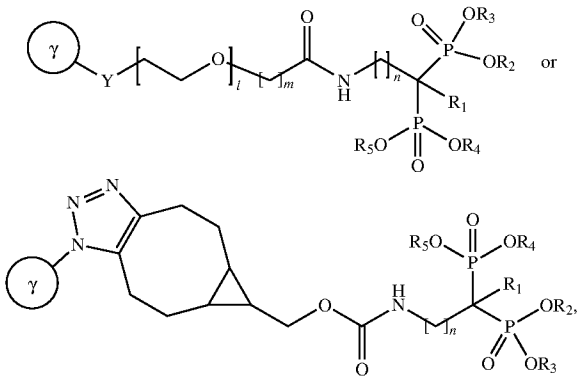

wherein γ (gamma) is a peptide or polypeptide activator of Glut1 or glucose uptake into osteoblasts, a peptide or polypeptide activator of insulin signaling in osteoblasts, a peptide or polypeptide inhibitor of gamma carboxylation (VKOR or GGCX), a peptide or polypeptide activator of EAAT1 or glutamate uptake into osteoblasts, a peptide or polypeptide inhibitor of glucocorticoid receptor activity in osteoblasts, a peptide or polypeptide activator of the hypoxia HIF signaling pathway (e.g., including inhibition of VHL and VEGFa signaling activation), or a peptide or polypeptide activator of Foxo1 signaling pathway in osteoblast, and wherein Y, when present, comprises a nitrogen of a side-chain of the native lysine residue and wherein Y is an alkylimine, an amide, a urea, thiourea, a sulfamidate, a substituted benzo[d][1,2,3]triazin-4(3H)-one, or a substituted 2-alkyliminoboronic acid.

A compound having the structure:

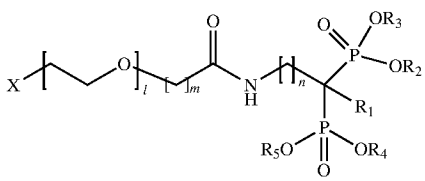

wherein $l = 0$ to $12$, $m = 0$ to $8$, and $n = 1$ to $10$ and $R_1$=H, OH, a halogen, CN, COOH, CONH$_2$, an alkyl ester, an optionally substituted alkyl, an optionally substituted aryl, or an optionally substituted heteroaryl and $R_2$, $R_3$, $R_4$, $R_5$ are each independently H, an optionally substituted alkyl, an optionally substituted aryl, or an optionally substituted heteroaryl and X=CHO, —N=C=S, —O—SO$_2$F, an NHS ester, a substituted ortho-carbonylboronic acid, a substituted ortho-(methoxycarbonyl)benzenediazonium, or 9-methoxybicyclo [6.1.0]non-4-yne.

Sarcopenia can be diagnosed using, e.g., JSH, AWGS, and EWGSOP2 criteria. In the JSH criteria, sarcopenia is defined as having low handgrip strength (<26 kg for males and <18 kg for females) and low muscle mass (<7.0 kg/m$^2$ for males and <5.7 kg/m$^2$ for females). In the AWGS criteria, sarcopenia is defined as having low handgrip strength (<26 kg for males and <18 kg for females) and/or low gait speed (≤0.8 m/s both for males and females) and low muscle mass (<7.0 kg/m$^2$ for males and <5.7 kg/m$^2$ for females). In the EWGSOP2 criteria, sarcopenia is defined as having low handgrip strength (<27 kg for males and <16 kg for females) and low muscle mass (<7.0 kg/m$^2$ for males and <5.5 kg/m$^2$ for females). Low gait speed (≤0.8 m/s both for males and females) is an indicator for defining 'severe sarcopenia'. Handgrip strength can be assessed with a digital grip strength dynamometer. Muscle mass can be assessed by the BIA method (InBody S10; InBody, Seoul, Korea). SMI can be calculated as the sum of the muscle mass of the four limbs divided by the height square (kg/m$^2$). Gait speed can be assessed over a predetermined distance, e.g. 6 m. BMD can be assessed at the lumbar spine (L2-L4), femoral neck, and total hip using, for example, DEXA (PRODIGY; GE Healthcare, Madison, WI, USA). Osteoporosis can be diagnosed according to the World Health Organization criteria (osteoporosis: T-score≤−2.5; osteopenia: T-score between −2.5 and −1.0; normal: T-score>−1.0).

In embodiments, the composition of the invention does not comprise a bisphosphonate attached via one of its non-phosphonate R groups through a linking portion containing only peptide bonds to an Interleukin-6. In embodiments, the composition of the invention does not comprise more than one protein or one peptide or polypeptide. In embodiments, the composition of the invention does not comprise an antibody, a fragment of an antibody or an scFv. In embodiments, the composition of the invention is not a fusion protein or fusion peptide. In embodiments, the composition of the invention is not an IL-6-bisphosphonate fusion peptide.

Bisphosphonates are known in the art and have the following general structure:

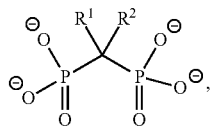

with $R^1$ and $R^2$ (i.e., $R^{superscript}$, not $R_{subscript}$) defined as below in Table 1.

TABLE 1 known bisphosphonates

| Class | Name | $R^1$ | $R^2$ | Relative potency (vs Etidronate = 1) |
|---|---|---|---|---|
| Non-nitrogenous | Etidronate (Didronel) | OH | $CH_3$ | 1 |
| | Clodronate (Bonefos, Loron) | Cl | Cl | 10 |
| | Tiludronate (Skelid) | H | p-Chlorophenylthio | 10 |
| Nitrogenous | Pamidronate (APD, Aredia) | OH | $(CH_2)_2NH_2$ | 100 |
| | Neridronate (Nerixia[a]) | OH | $(CH_2)_5NH_2$ | 100 |
| | Olpadronate | OH | $(CH_2)_2N(CH_3)_2$ | 500 |
| | Alendronate (Fosamax) | OH | $(CH_2)_3NH_2$ | 500 |
| | Ibandronate (Boniva - US, Bonviva - Asia) | OH | $(CH_2)_2N(CH_3)(CH_2)_4CH_3$ | 1000 |
| | Risedronate (Actonel) | OH | 3-Pyridylmethyl | 2000 |
| | Zoledronate (Zometa, Aclasta) | OH | 1H-imidazol-1-ylmethyl | |

In embodiments, the cytokine-bisphosphonate conjugate, or IL6-BP conjugate, disclosed herein is lyophilized and/or freeze dried and are reconstituted for use. Compositions or pharmaceutical compositions comprising the IL6-BP disclosed herein can comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection or infusion, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of IL6-BP in solution and is suitable for inhalational or parenteral administration. In an embodiment, the composition or pharmaceutical composition is suitable for intravenous, intramuscular, intraperitoneal, intradermal, intraorgan, and/or subcutaneous injection. In an embodiment, the composition or pharmaceutical composition is in liquid form and has minimized risk of bubble formation and a naphylactoid side effects. In an embodiment, the composition or pharmaceutical composition is isotonic. In an embodiment, the composition or pharmaceutical composition has a pH or 6.8 to 7.4.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

In an embodiment the composition or pharmaceutical composition comprising the IL6-BP described herein is substantially pure with regard to the IL6-BP. A composition or pharmaceutical composition comprising the IL6-BP described herein is "substantially pure" with regard to the IL6-BP when at least 60% to 75% of a sample of the composition or pharmaceutical composition exhibits a single species of the IL6-BP. A substantially pure composition or pharmaceutical composition comprising the IL6-BP described herein can comprise, in the portion thereof which is the IL6-BP, 60%, 70%, 80% or 90% of the IL6-BP, more usually about 95%, and preferably over 99%. Purity or homogeneity may be tested by a number of means well known in the art, such as polyacrylamide gel electrophoresis or HPLC.

Administration can be local. Administration can be performed in a manner so as to not elicit systemic effects. Administration can be intramuscular or subcutaneous. Administration can be via infusion or injection. Administration can be oral or parenteral.

In non-limiting embodiments, the IL6-BP, or other listed cytokine-BP conjugate, is administered twice daily, daily, every other day, weekly, monthly or every three months. In embodiments, the IL6-BP, or other listed cytokine-BP conjugate, is administered every six months or yearly. In embodiments, the IL6-BP, or other listed cytokine-BP conjugate, is administered once to the subject.

In non-limiting embodiments, dosages of the conjugate disclosed of the methods herein are 0.0025 ng/g to 3.0 ng/g; 0.0050 ng/g to 1.5 ng/g; or 0.0075 ng/g to 1.0 ng/g of body weight, for example, for a human subject. In non-limiting embodiments, dosages of the conjugate disclosed of the methods herein are 0.08 ng/g of body weight; 0.025 ng/g of body weigh; or 0.008 ng/g of body weight for a human subject.

Also provided is an IL-6 family cytokine conjugated to a polyaspartate peptide chain that targets the IL-6 family cytokine to bone. In embodiments, the IL-6 family cytokine is Interleukin-6. In embodiments, the interleukin-6 has the sequence of a human Interleukin-6. In embodiments, the poly-aspartate peptide is an $(Asp)_6$. In embodiments, the poly-aspartate peptide is an $(L-Asp)_6$. In embodiments, the poly-aspartate peptide is joined to the IL-6 family cytokine by a peptide bond.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

Definitions: The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means a mammal. Mammals include canines, felines, rodents, bovine, equines, porcines, ovines, and primates including humans. Thus, the invention can be used in human medicine or also in veterinary medicine, e.g., to treat companion animals, farm animals, laboratory animals in zoological parks, and animals in the wild. The invention is particularly desirable for human medical applications. In a preferred embodiment the subject is a human.

The terms "treat", "treatment" of a disease or condition, and the like refer to slowing down, relieving, ameliorating or alleviating at least one of the symptoms of the sarcopenia or reduced exercise capacity, or reversing the disease after its onset.

The term "in need thereof" with regard to a subject would be a subject known or suspected of having or being at risk of developing a sarcopenia or reduced exercise capacity.

The terms "therapeutically effective amount" or "amount effective to" encompasses an amount sufficient to ameliorate or inhibit a symptom or sign of the medical condition. An effective amount for a particular subject may vary depending on factors such as the condition being treated, the overall health of the patient, the method route and dose of administration and the severity of side effects. An effective amount can be the maximal dose or dosing protocol that avoids significant side effects or toxic effects. In embodiments, a therapeutically effective amount of IL6-BP is administered.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

During exercise, a feed-forward loop between osteocalcin from bone and IL-6 from muscle stimulates the release of both hormones and is required for normal exercise capacity.

According to an exemplary embodiment of the present disclosure, the engineering of an IL-6 bisphosphonate fusion protein (IL-6-BP) that targets sustained IL-6 signaling exclusively to bone can be provided. According to an exemplary embodiment of the present disclosure, it has been found that treatment of old mice but not young mice with IL-6-BP dramatically increases their exercise capacity (distance run on a treadmill at 30 cm/s until exhaustion). Furthermore, a single dose of IL-6-BP produces an increase in exercise capacity in aged mice that lasts at least 6 days, making it a very promising drug candidate. The exemplary 1st generation IL-6-BP is a heterogeneous mixture with bisphosphonates attached to 1, 2 or 3 of the 14 lysines located in the IL-6 peptide.

According to an exemplary embodiment of the present disclosure, an optimized 2nd generation IL-6-BP can be engineered using genetic code expansion in combination with bioorthogonal click chemistry. This can produce 2nd generation IL-6-BPs with bisphosphonate at highly specific location in the IL-6 peptide. A lead 2nd generation IL-6-BP candidate can be selected based on their activity and affinity.

According to an exemplary embodiment of the present disclosure, it can be determined the extent of the ability of 2nd generation IL-6-BP to restore exercise capacity in aged mice without any side effect on other tissues. According to an exemplary embodiment of the present disclosure, can be established a new class of drug, IL-6-BPs that can produce a long-lasting restoration of exercise capacity in the aged animals.

Few manifestations of aging are more devastating to individuals than the decline/loss of exercise capacity. This decline/loss with age affects quality of life and has deleterious effects on many other physiologies. Many therapeutic approaches have sought to improve exercise capacity (1). None have worked to the degree required to improve health in aged patients.

Osteocalcin (OCN) is a bone-derived hormone, which declines precipitously with age and is required for muscle function during exercise (2). Its short half-life hinders the development of OCN itself as a drug. To overcome this inherent limitation, according to an exemplary embodiment of the present disclosure a fusion protein can be engineered that harnesses OCN biology and can reverse age-related decline in exercise capacity.

Figure 9A:
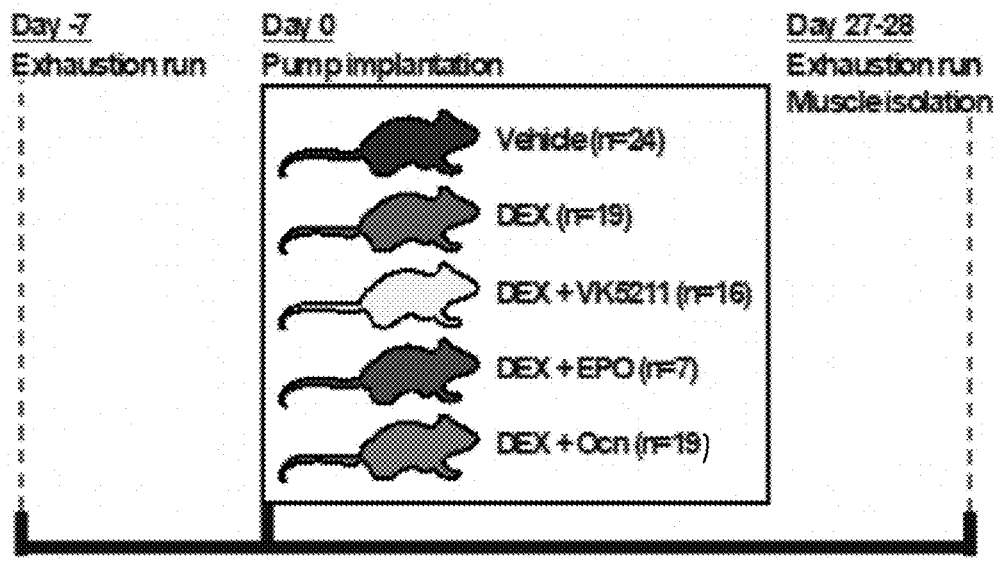
FIG. 9A-9C are exemplary graphs showing that OCN prevents DEX-induced loss of exercise capacity.
Figure 9B:
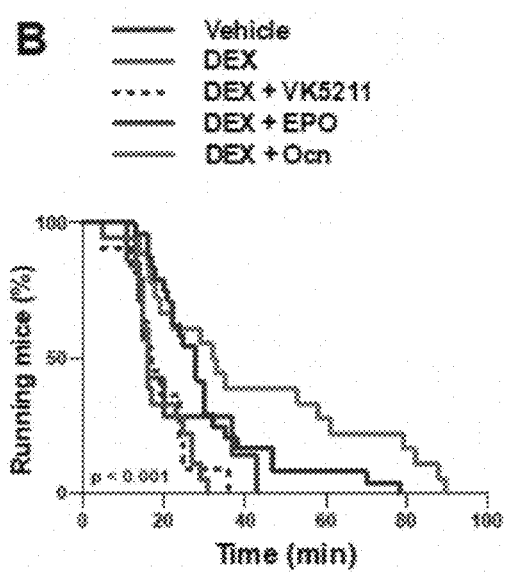
Figure 9C:
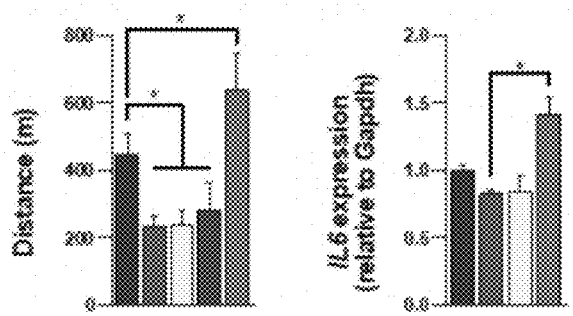

During exercise, OCN is released from bone into the blood stream, signals through its receptor Gprc6a, in muscle increases glucose and fatty acid uptake and catabolism and thus ATP production (3). Accordingly, continuous replenishment of OCN in 12-month old mice restores their exercise capacity to that of 3-month old mice (3). Furthermore, according to an exemplary embodiment of the present disclosure, it has been determined that OCN continuously delivered by pump can also prevent glucocorticoid (DEX)-induced decline in endurance exercise (Run on a treadmill at 30 cm/s until exhaustion) (FIGS. 9A-9C). While OCN's physiological effects hold therapeutic promise for the treatment of age-related decline in exercise capacity, its short half-life in blood since it is a peptide hormone, hinders a drug development strategy.

OCN release during exercise can be coordinated by a feed-forward loop. During exercise, OCN is required for the release of IL-6 from muscle and IL-6 is required for the release of OCN from bone (4). Accordingly, mice lacking the IL-6 receptor exclusively in bone exhibit a severe deficit in exercise capacity (4). According to an exemplary embodiment of the present disclosure, IL-6 signaling can be increased exclusively in bone, and this can reverse age-related decline in exercise capacity without eliciting any negative side-effects of IL-6 in the immune system.

In an exemplary embodiment of the present disclosure, IL-6 can be targeted to bone by conjugating it to alendronate (IL-6-BP). Alendronate, a bisphosphonate (BP), has three exemplary defining characteristics: 1] exclusive affinity for mineralized bone, 2] it inhibits osteoclastic bone loss and 3] it adheres to bone for weeks. Alendronate is an FDA approved drug that is the primary tool to treat age-related osteoporosis. Of note, the equimolar bioactive dose of BP in IL-6-BP is 100-fold less than the dose for osteoporosis (5). Thus, alendronate should enable a sustained increase of IL-6 signaling exclusively in bone, which should stimulate long-lasting increase in exercise capacity.

The exemplary embodiments of the present disclosure are illustrated herein by the following examples, which should not be construed as limiting. The contents of all references, pending patent applications and published patents, cited throughout this application are hereby expressly incorporated by reference. Those skilled in the art will understand that these exemplary embodiments of the present disclosure may be embodied in many different forms and should not be construed as limited to the embodiments set forth herein. Rather, these exemplary embodiments are provided so that the present disclosure will fully convey the exemplary embodiment of the present disclosure to those skilled in the art. Various exemplary modifications and other exemplary embodiments of the present disclosure will come to mind in one skilled in the art to which this invention pertains having the benefit of the teachings presented in herein. Although specific terms are employed, they are used as in the art unless otherwise indicated.

Example 1

Avoiding the constraint that the short, 15 minutes-long half-life of OCN protein has, the regulation of osteocalcin by IL-6 could be an excellent path to chronically raise circulating osteocalcin without having to inject daily or rely on minipumps. To avoid the severe inflammatory events the presence of IL-6 in the general circulation would cause, we conjugated IL-6 to alendronate (ALN) (IL6-BP). As a bisphosphonate-targeted molecule, ALN has a high affinity for the bone ECM, remains in the bone ECM for weeks.

Figures 10A, 10B, 10C, 10D, 10E, 10F, 10G:
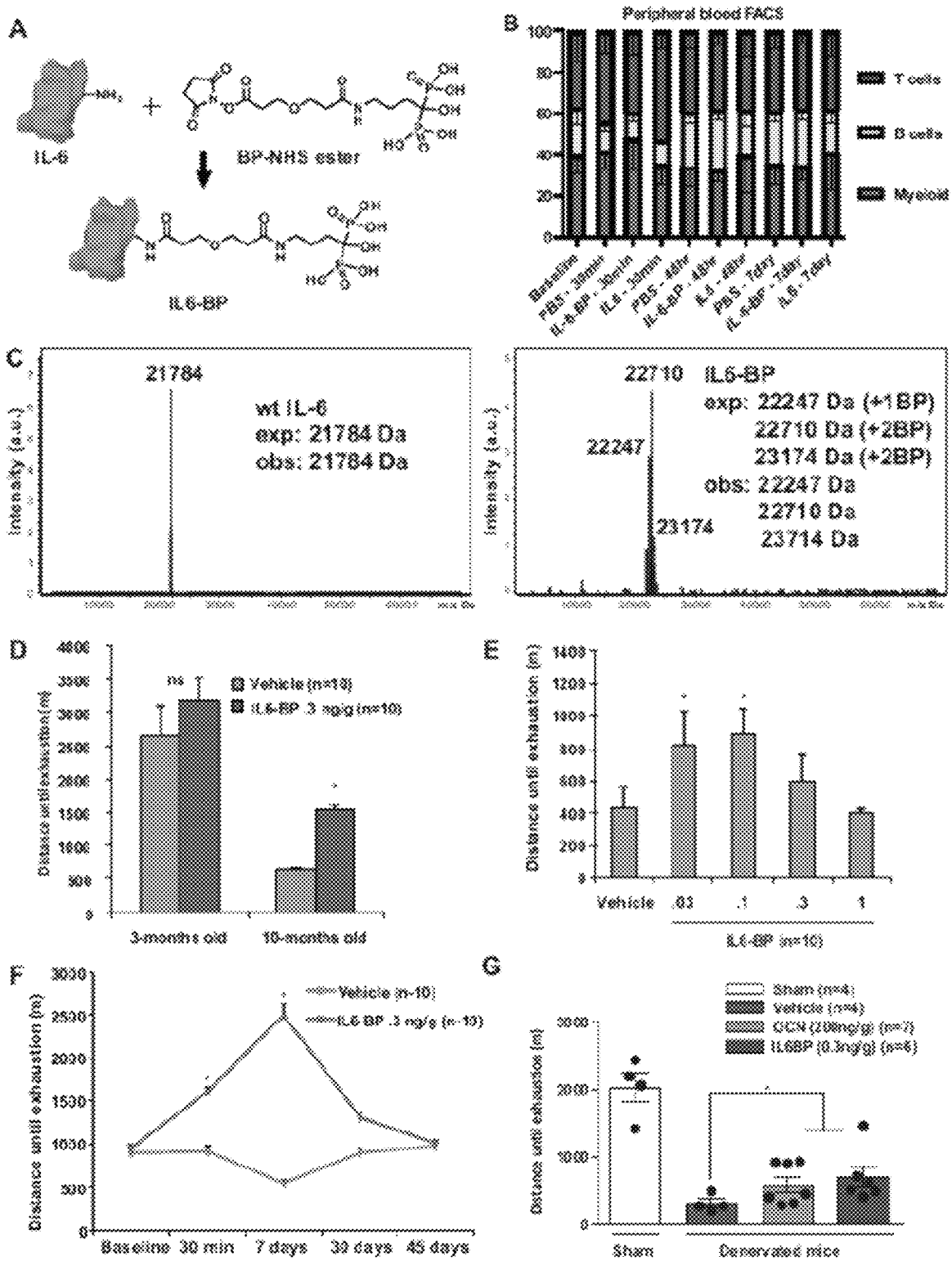
FIG. 10A-10G. IL6-BP increases exercise capacity in aged mice. 10A) Generation of $1^{st}$ generation IL6-BP by conjugating aminated BP with a PEG linker to 1, 2, or 3 of the 14 lysines in IL-6. 10B) FACS analysis of blood cells before, 30 min, and 48 hours after injection of 0.3 ng/g IL6-BP, (n=10) 10C) Mass spectrometry evidence of IL-6 conjugation to aminated BP. 10D) Exercise capacity in 3- or 10-months-old WT mice 30 minutes after i.p. injection of IL6-BP (0.3 ng/g) (n=10). 10E) Exercise capacity in 10-months-old WT mice 30 minutes after injection of vehicle or 0.03, 0.1, 0.3, 1 ng/g IL6-BP, n=10. 10F) Exercise capacity in 10-months-old at baseline, 30 mins, 7, 14, 30 or 45 days after i.p. injection of vehicle or IL6-BP (0.3 ng/g) (n=10). 10G) Exercise capacity in denervated and sham-operated mice 30 mins after injection of 0.3 ng/g IL6-BP, (n=7).

This 1st generation IL-6-BP was engineered by crosslinking an aminated pegylated BPs to 1, 2, or 3 of the 14 lysine residues in IL-6 (FIG. 10A) crosslinking an N-hydroxysuccinimide (NHS) ester-labeled BP to the lysine residues of IL 6 protein (FIG. 10A-C). A single injection of IL-6-BP (i.p., 0.3 ng/g) doubled exercise capacity in 12-month old mice but had little to no effect on young (3-month old) mice. Remarkably, and unlike what was observed after a single injection with OCN, the massive increase in the exercise capacity after injection with IL-6-BP endures for up to 8 days (FIG. 10F). Thus, the exemplary data show that IL-6-BP substantially increases exercise capacity in an age specific manner and with a long duration of action. To verify that IL6-BP was targeted only to the bone ECM we analyzed myelopoiesis in the bone marrow, the tissue closest to the bone ECM and that is responsive to IL-6. We found that injections of IL6-BP did not affect myelopoiesis while it increased exercise capacity suggesting that IL6-BP selectively increases IL-6 signaling in osteoblasts (FIG. 10B).

IL6-BP induces a long-lasting increase in exercise capacity in an osteocalcin-dependent manner. In a proof of principle experiment, we tested the efficacy of this new hybrid molecule in wildtype (WT) mice that were either 3 months- (high circulating osteocalcin levels) or 10 months-old (low circulating osteocalcin). We injected either vehicle or IL6-BP (0.1 ng/g of body weight) in female WT mice. Thirty minutes later, these mice were placed on a treadmill and tested through an exhaustion run. We found that IL6-BP has a mild beneficial effect in 3 months-old mice but allowed 10 months-old mice to run twice if vehicle-treated mice (FIG. 10D). This effect of first generation IL6-BP was dose dependent with the most effective dose observed being 0.1 ng/g of body weight (FIG. 10E). To test the durability of the effect of IL6-BP, we ran again 10 months-old mice 7 days after injection and the IL6-BP-treated mice ran 3 times longer than vehicle treated-treated littermates (FIG. 10F). We ran again these groups of mice 30 days post-injection and observed that IL6-BP-treated 10 months-old mice were still running 40% more, than vehicle treated control mice (FIG. 10F). This difference had disappeared by day 45 post-injection. To determine if IL6-BP favors exercise capacity in an osteocalcin-dependent manner, we injected IL6-BP into Osteocalcin−/− mice.

Figure 11A:
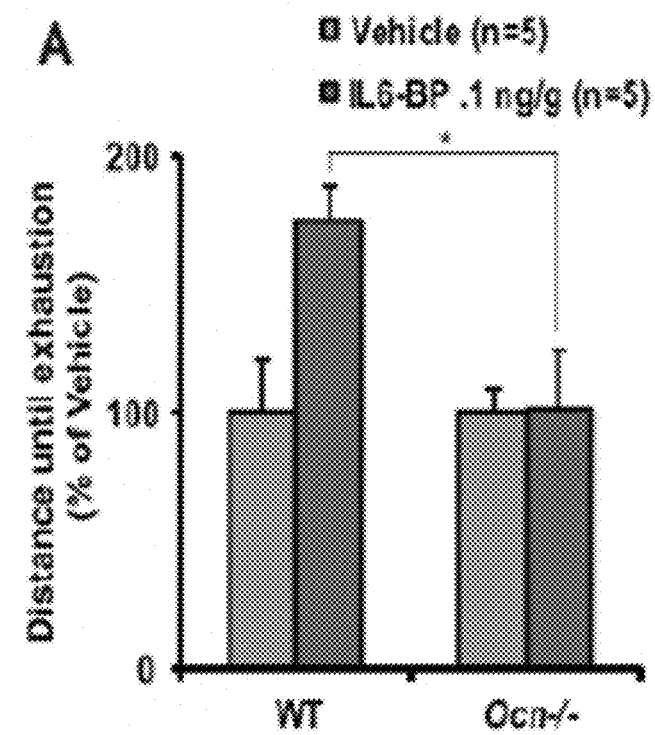
FIG. 11A-11B: IL6-BP increases exercise capacity in an osteocalcin-dependent manner. 11A) Exercise capacity in WT and Ocn−/− mice 30 minutes after injection of 0.3 ng/g IL6-BP, n=5. 11B) Serum uncarboxylated osteocalcin at indicated times after injection of vehicle 0.3 ng/g IL6-BP or 0.3 ng/g IL6 (n=5). *, p<0.05 by Student's t-test or two-way ANOVA with Bonferroni correction.
Figure 11B:
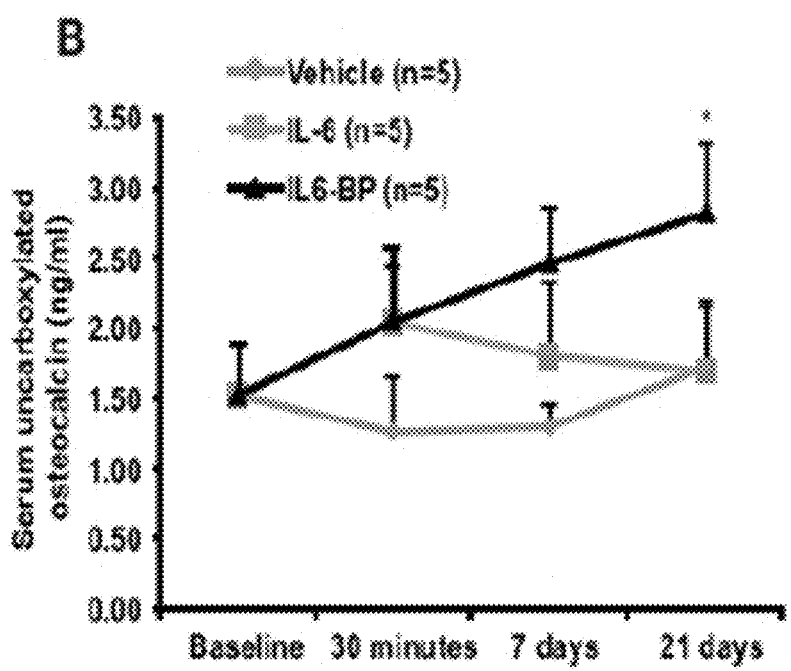

As shown in FIG. 11A, IL6-BP failed to increase exercise capacity in Osteocalcin−/− mice as it does in WT mice. Furthermore, injection of IL6-BP but not of vehicle or IL-6, triggers a sustained increase in osteocalcin levels that lasts for at least 21 days (FIG. 11B). These preliminary results support the notion that IL6-BP enhances exercise capacity because it increases circulating osteocalcin.

Figures 12A, 12B, 12C:
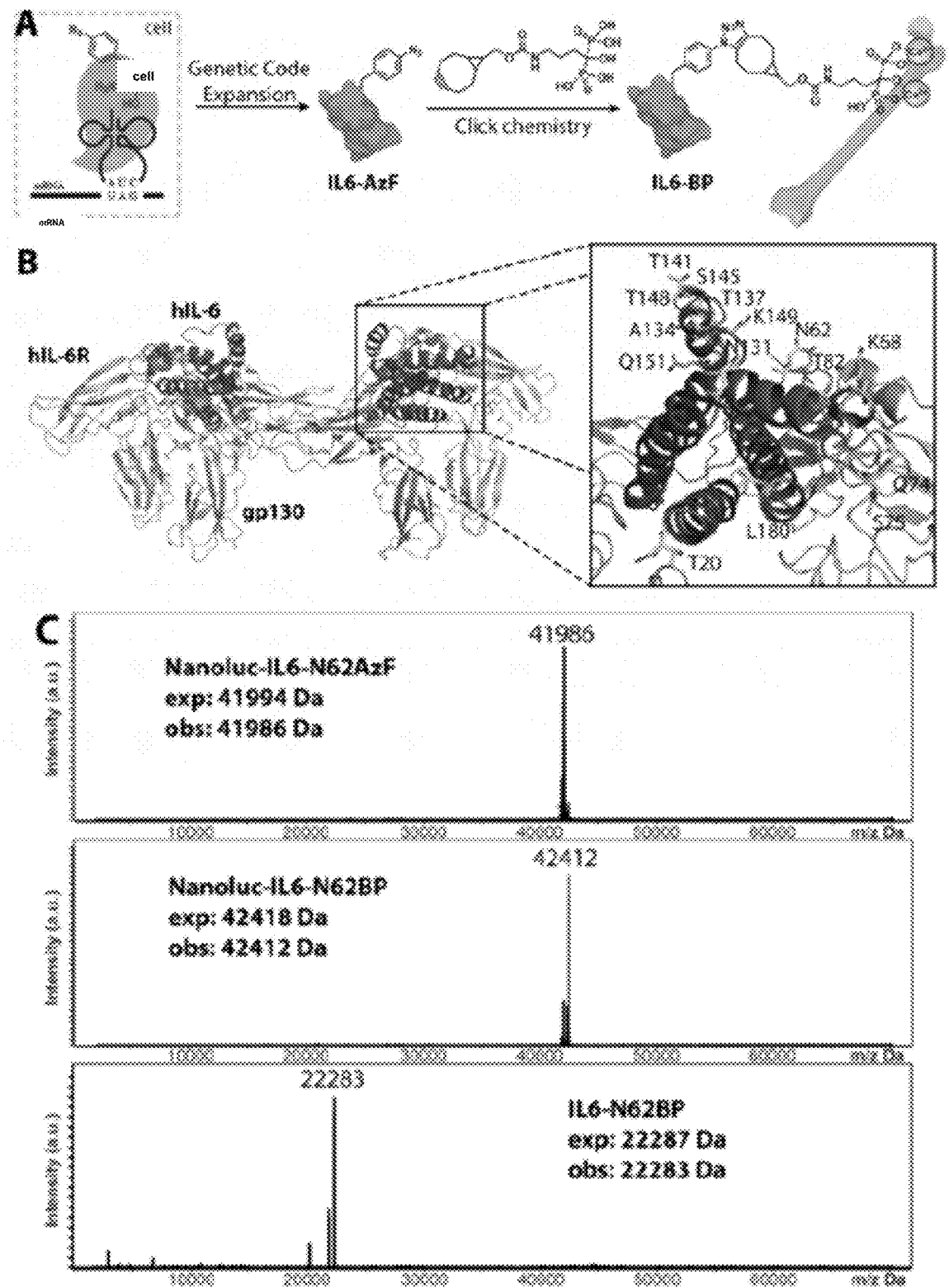
FIG. 12A-12C: 12A) Preparation of IL6-BP using the Genetic Code Expansion. 12B) Co-crystal complex of IL-6 (blue), IL-6R (pink), and gp130 (brown). 19C) ESI-MS analysis of Nanoluc-IL6-N62AzF, Nanoluc-IL6-N62BP, and IL6-N62BP.
Figure 13:
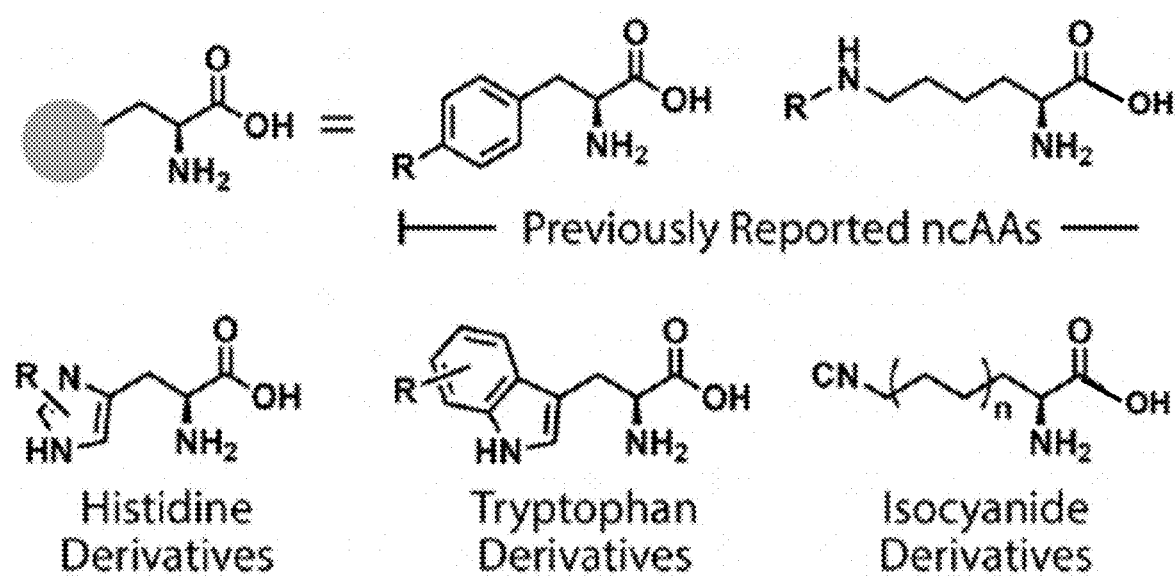
FIG. 13: Structures of non-canonical amino acids (ncAAs) that were site-specifically incorporated into proteins using the Genetic Code Expansion technology. In embodiments any one of these ncAAs can be used in place of the azidophenylalanine in the examples hereinbelow.
Figures 14A, 14B, 14C:
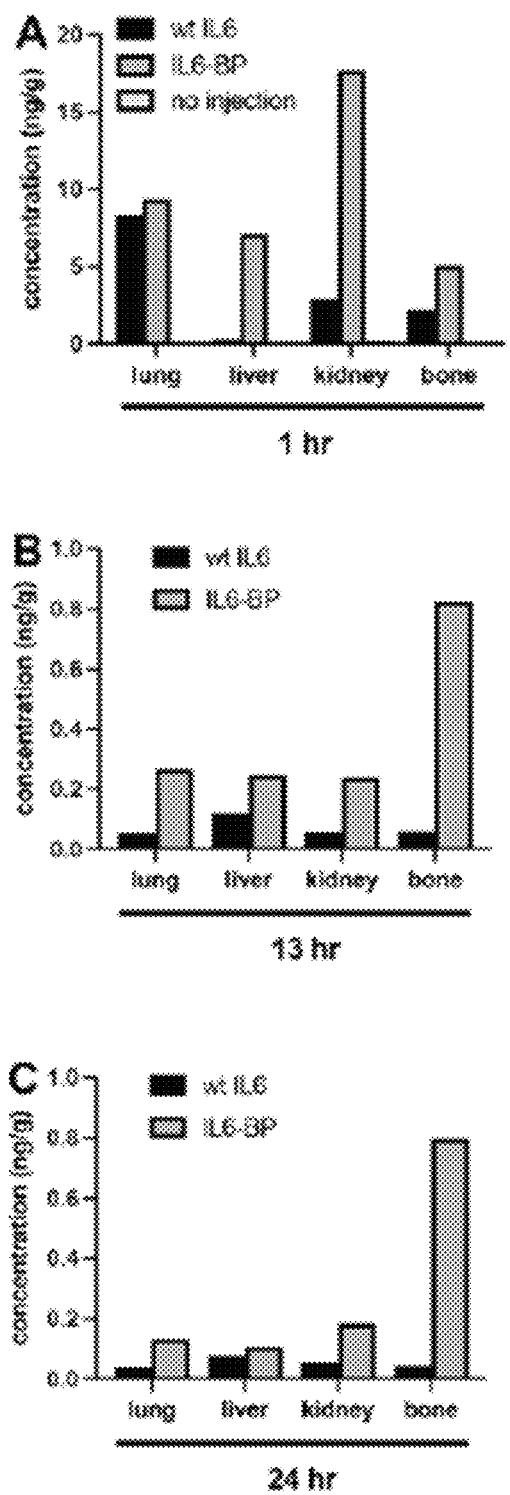
FIGS. 14A-14C: Differential bone targeting ability of wild type IL-6 (wt IL-6) and (human) IL6-BP conjugate. Comparison of the biodistribution profiles of IL-6 and human IL-6BP conjugate in C57/B6 mice 1 h (14A), 13 h (14B), and 24 h (14C), after injection of IL-6 or IL6-BP conjugate. Levels measured by specific ELISA.

Collectively, our data demonstrate on the one hand, that osteocalcin can prevent the appearance of Dex-induced loss of muscle function in middle-aged mice and partially rescue the denervation-induced loss of muscle function in mice. On the other hand, a single injection of IL6-BP can increase, for up to 30 days, exercise capacity in middle-aged WT mice in an osteocalcin-dependent manner Example 2: Engineer a 2nd Generation IL-6-BP The 1st generation IL-6-BP is a heterogeneous unoptimized mixture. A homogenous and optimized 2nd generation IL-6-BP can be generated using genetic code expansion in combination with bioorthogonal click chemistry. For example, Azidophenylalanine (AzF) can be site-specifically incorporated into IL-6 in response to an amber codon at one of several locations (e.g., Phe9, Phe14, Phe25, Tyr46, Thr20, Lys68, Glu74, Ser75, Thr82, Asn131, Ala134, Thr137, Thr141, Ser145, Thr148, Lys149, Glu151, or Leu180) by, for example, an orthogonal aminoacyl-tRNA synthetase (aaRS)/tRNA pair in *E. coli* (FIG. 12A). The purified AzF-containing IL-6 can be functionalized using bicyclo [6.1.0] nonyne-alendronate.

IL-6 activates it signaling pathway via assembling a complex of IL-6, the IL-6 receptor (IL-6R), and a shared signaling receptor gp130 (58). To avoid that a non-selective labeling of IL-6 with ALN disrupts its binding to IL-6R or gp130, and diminishes the biological activity of IL-6, we will site-specifically introduce a noncanonical amino acid, azido phenylalanine (AzF) into solvent exposed residues of IL-6 in response to an amber codon using orthogonal aminoacyl-tRNA synthetase (aaRS)/tRNA pairs in *E. coli* (FIG. 12A). To demonstrate the successful preparation of IL-6 with BP modification at distinct residues, we have used a newly developed nanoluciferase (Nanoluc) as an N-terminal fusion partner to achieve the soluble overexpression of the IL-6 (59). Briefly, AzF was first site-specifically incorporated at Asn62 position of Nanoluc-IL6 fusion protein (FIGS. 12B and 12C). The purified AzF-containing Nanoluc-IL6-N62AzF will be subsequently functionalized using bicyclo [6.1.0] nonyne-alendronate (BCN-ALN), followed by the cleavage of Nanoluc using Tobacco Etch Virus Protease. ESI-MS analysis confirmed the site-specific modification of BP at Asn62 residue of IL-6 (FIG. 12C). Next, we will prepare IL-6 mutants with ALN at residues as distant as possible from the binding sites of IL-6R and gp130, e.g., Thr20, Lys68, Glu74, Ser75, Thr82, Asn131, Ala134, Thr137, Thr141, Ser145, Thr148, Lys149, Glu151, and Leu180 (FIG. 12B). The successful generation of these IL-6 mutant molecules can be confirmed by SDS-PAGE and ESI-MS.

Evaluation of the activity of the second generation IL6-BP in vitro. Quantification of bone-targeting affinity of IL6-BP. To quantify the affinity difference among the bone-targeting IL-6 mutants, we will incubate IL-6 mutants with ALN attached to various residues (prepared above) with HA or native bone. The binding percentage will be calculated as follow, where OD represents optical density: [(ODwithout HA−ODwith HA)/(ODwithout HA)]×100%. Next, FITC-labeled IL-6, and FITC-labeled IL-6-BP mutants will be further used to stain non-decalcified mouse bone sections. Robust FITC signal is expected in sections stained with the IL6-BP mutant, but not in the ones stained with native IL-6. Determination of the activity of bone-targeting IL-6 mutants. To ensure that the introduction of bone-homing moiety brings minimum perturbation to IL-6 function, the EC50s are determined of IL-6 mutants using IL-6 reporter cells (HEK-Blue IL-6; InvivoGen).

Cells will be seeded at $8 \times 10^5$ cells/mL in a 96-well plate, 20 μL of IL6-BP mutants or WT IL-6 will be added. After 24 hours, IL-6-induced secreted alkaline phosphatase will be measured with QUANTI-Blue (Invivogen). The EC50s of IL-6 mutants will be identified using Prism from GraphPad.

In vivo disposition study of second generation IL6-BP. In vivo pharmacokinetics studies of bone-targeting IL-6 mutants. C57/B6 mice (4 weeks-old) will be randomly divided into 3 groups for each study (n: 10 per group and per sex). WT IL-6 (0.1 ng/g of body mass in PBS), second generation IL6-BP (same regimen as IL-6), or PBS buffer will be administered to mice i.p. At various time points (½, 1, 2-, 4-, 8-, and 16-days post injection), blood samples will be collected from the tail vein. Circulating IL-6 levels will be measured by ELISA. A total of 30 animals will be required for this study.

In vivo Biodistribution Studies of Bone-Targeting IL-6. Even though radiolabeling remains the gold standard for quantifying bulk organ and tissue distribution, recent study suggests that AF680 exhibits similar clearance and tissue distribution to unlabeled Tras over 17 days (60). Thus, AF680 fluorescent dye will be used in this study. AF680 modified WT IL-6 (0.1 ng/g of body mass in PBS), IL6-BP (same regimen as IL-6) will be administered i.p. to C57/B6 mice (4 weeks). Mice will be sacrificed at 1, 2-, 4-, 8-, 16-, and 32-days post injection, and the heart, liver, spleen, lung, kidney, and vertebrae excised for fluorescence imaging, histology, and bone histomorphometry. Each group will include 20 animals (10 males, 10 females) and a total of 240 animals will be required for this study.

Example 3

Establish the ability of IL-6-BP to reverse age-related decline in muscle function. We have gathered evidence, already presented herein, that first generation IL6-BP can increase exercise capacity in 10 months-old, i.e., middle aged WT mice. For the second generation IL-6-BP, a similar protocol can be followed. For example, IL-6-BP (0.3 ng/g) will be injected in 12 months-old wildtype (WT) mice WT or as negative controls in those lacking the osteocalcin receptor. After 8, 12, 16, 20 and 28 days, OCN serum levels and exercise capacity will be determined. It may be anticipated that IL-6-BP will increase exercise capacity in WT but not mutant mice. This will also establish the minimum required dosing frequency, which, based on preliminary data, can be 8 days.

IL6-BP, unconjugated IL-6 or vehicle will then be injected at the established dose and frequency for 1 month in 3-, 12-18- and 24-months-old mice and exercise capacity determined. IL-6-BP efficacy will be tested in the model of DEX-induced decline in exercise capacity (FIG. 9A). It may be confirmed that IL6-BP localizes exclusively to bone by mass spectrometry and that IL-6-BP does not cause adverse effects in the immune system by measuring body temperature, blood CRP, TNFa and IL-1a and cardiomyocyte apoptosis by histology (6, 7).

Finally, to elucidate IL-6-BP mechanism of action, RNAseq may be performed in muscle of 3- and 24-month old mice 4 hours after IL-6-BP or vehicle injection.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that

REFERENCES

1. Cohen S, Nathan J A, Goldberg A L. Muscle wasting in disease: molecular mechanisms and promising therapies. Nat Rev Drug Discov. 2015; 14(1):58-74.
2. Karsenty G, Olson E N. Bone and muscle endocrine functions: unexpected paradigms of inter-organ communication. Cell. 2016; 164(6):1248-56.
3. Mera P, Laue K, Ferron M, Confavreux C, Wei J, Galan-Diez M, et al. Osteocalcin Signaling in Myofibers Is Necessary and Sufficient for Optimum Adaptation to Exercise. Cell Metab. 2016; 25(1):218.
4. Chowdhury S, Schulz L C, Palmisano B, Singh P, Berger J M, Yadav V K, et al. Muscle derived interleukin-6 increases exercise capacity by signaling in osteoblasts. J Clin Invest. 2020.
5. Azuma Y, Sato H, Que Y, Okabe K, Ohta T, Tsuchimoto M, et al. Alendronate distributed on bone surfaces inhibits osteoclastic bone resorption in vitro and in experimental hypercalcemia models. Bone. 1995; 16(2):235-45.
6. Pedersen B K, Febbraio M A. Muscles, exercise and obesity: skeletal muscle as a secretory organ. Nat Rev Endocrinol. 2012; 8(8):457-65.
7. Mihara M, Hashizume M, Yoshida H, Suzuki M, Shiina M. IL-6/IL-6 receptor system and its role in physiological and pathological conditions. Clin Sci (Lond). 2012; 122 (4):143-59.

The invention claimed is:

1. A cytokine-bisphosphonate conjugate having the structure:

a)

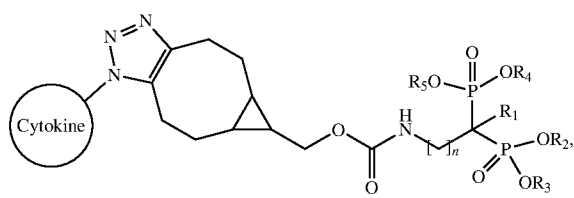

wherein
the cytokine comprises an azidophenylalanine residue, wherein the triazole set forth above is composed from an azide group of the azidophenylalanine residue, and wherein $n = 1$ to 10, $R_1$=H, OH, a halogen, CN, COOH, CONH$_2$, an alkyl ester, an alkyl, an aryl, or a heteroaryl, and
$R_2$, $R_3$, $R_4$, and $R_5$ are each independently H, alkyl, aryl, or a heteroaryl;

or b)

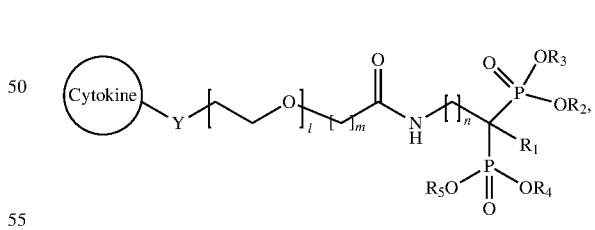

wherein
the cytokine comprises a native lysine residue, and wherein Y comprises a nitrogen of a sidechain of the native lysine residue and wherein Y is an alkylimine, an amide, a urea, thiourea, a sulfamidate, a substituted benzo[d][1,2,3]triazin-4(3H)-one, or a substituted 2-alkyliminoboronic acid,
and wherein
when Y is an alkylimine, the bisphosphonate is attached via an imine carbon atom and the cytokine is attached at a nitrogen atom of the alkylimine, or when Y is an amide, the bisphosphonate is attached via a carbonyl carbon atom of the amide and the cytokine is attached at a nitrogen atom of the amide, or when Y is a urea, the bisphosphonate is attached to one of the nitrogen atoms thereof and the cytokine is attached at the other nitrogen atom of the urea, or when Y is a thiourea, the bisphosphonate is attached to one of the nitrogen atoms thereof and the cytokine is attached at the other nitrogen atom of the thiourea, or when Y is a sulfamidate, the bisphosphonate is attached at one of the oxygen atoms thereof, and the cytokine is attached at a nitrogen atom of the sulfamidate, or when Y is a substituted benzo[d][1,2,3]triazin-4(3H)-one, the bisphosphonate is attached at the 5, 6, 7, or 8 position and the cytokine is attached at the nitrogen atom alpha to the carbonyl, and wherein l=0 to 12, m=0 to 8, and n=1 to 10;

or a pharmaceutically-acceptable salt thereof, wherein the cytokine is IL-6, Leptin, IL-11, ciliary neurotrophic factor (CNTF), leukemia inhibitory factor (LIF), oncostatin M (OSM), cardiotrophin 1 (CT-1), cardiotrophin-like cytokine (CLC), or IL-27.

2. The cytokine-bisphosphonate conjugate of claim 1, wherein $R_1$ is OH, and n=1, and $R_2$, $R_3$, $R_4$, and $R_5$ are each independently H, and the cytokine comprises the azidophenylalanine residue.

3. The cytokine-bisphosphonate conjugate of claim 1, wherein $R_1$ is OH, and $R_2$, $R_3$, $R_4$, and $R_5$ are each independently H, and l=1, m=2, n=3, and Y is an amide and the cytokine comprises the native lysine residue.

4. The cytokine-bisphosphonate conjugate of claim 1, wherein the azidophenylalanine is incorporated at (a) a Phe9, Phe14, Phe25, Tyr46, Thr20, Lys68, Glu74, Ser75, Thr82, Asn131, Ala134, Thr137, Thr141, Ser145, Thr148, Lys149, Glu151, or Leu180 residue of the IL-6, or (b) a Phe9, Phe14, Phe25, Thr48, Lys69, Ser 75, Asn131, Ala140, Ser146, Thr 147, Lys150, or Leu179 residue of the IL-6.

5. A cytokine-6-bisphosphonate conjugate comprising the following molecule, or pharmaceutically acceptable salt thereof, wherein IL-6 is an interleukin-6:

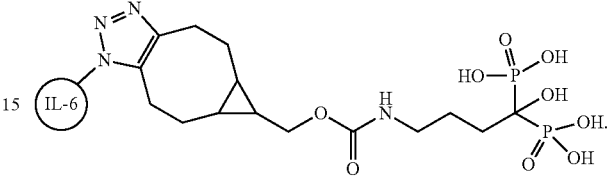

6. The cytokine-bisphosphonate conjugate of claim 5, wherein the azidophenylalanine is functionalized with a bicyclo[6.1.0]nonyne-bisphosphonate.

7. A cytokine-bisphosphonate conjugate, comprising the following molecule, or pharmaceutically acceptable salt thereof, wherein IL-6 is an interleukin-6:

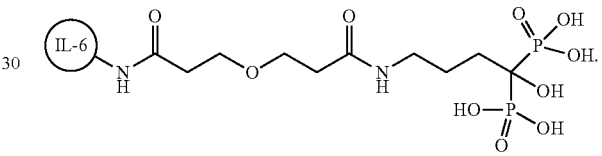

* * * * *

```
                             SEQUENCE LISTING

Sequence total quantity: 2
SEQ ID NO: 1               moltype = AA    length = 212
FEATURE                    Location/Qualifiers
source                     1..212
                           mol_type = protein
                           organism = Homo sapiens
SEQUENCE: 1
MNSFSTSAFG PVAFSLGLLL VLPAAFPAPV PPGEDSKDVA APHRQPLTSS ERIDKQIRYI    60
LDGISALRKE TCNKSNMCES SKEALAENNL NLPKMAEKDG CFQSGFNEET CLVKIITGLL   120
EFEVYLEYLQ NRFESSEEQA RAVQMSTKVL IQFLQKKAKN LDAITTPDPT TNASLLTKLQ   180
AQNQWLQDMT THLILRSFKE FLQSSLRALR QM                                 212

SEQ ID NO: 2               moltype = AA    length = 212
FEATURE                    Location/Qualifiers
source                     1..212
                           mol_type = protein
                           organism = Homo sapiens
SEQUENCE: 2
MNSFSTSAFG PVAFSLGLLL VLPAAFPAPV PPGEDSKDVA APHRQPLTSS ERIDKQIRYI    60
LDGISALRKE TCNKSNMCES SKEALAENNL NLPKMAEKDG CFQSGFNEET CLVKIITGLL   120
EFEVYLEYLQ NRFESSEEQA RAVQMSTKVL IQFLQKKAKN LDAITTPDPT TNASLLTKLQ   180
AQNQWLQDMT THLILRSFKE FLQSSLRALR QM                                 212
```